(12) United States Patent
Banik

(10) Patent No.: US 9,199,045 B2
(45) Date of Patent: Dec. 1, 2015

(54) ADDITIVE FORCE DEVICE FOR DRUG DELIVERY PEN FOR INTRADERMAL MEDICATION INJECTION

(75) Inventor: Robert Banik, Long Valley, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 601 days.

(21) Appl. No.: 13/127,431

(22) PCT Filed: Nov. 17, 2009

(86) PCT No.: PCT/US2009/006146
§ 371 (c)(1),
(2), (4) Date: Jun. 23, 2011

(87) PCT Pub. No.: WO2010/056367
PCT Pub. Date: May 20, 2010

(65) Prior Publication Data
US 2011/0257604 A1 Oct. 20, 2011

Related U.S. Application Data

(60) Provisional application No. 61/193,314, filed on Nov. 17, 2008.

(51) Int. Cl.
*A61M 5/00* (2006.01)
*A61M 5/48* (2006.01)
*A61M 5/20* (2006.01)
*A61M 5/24* (2006.01)
*A61M 5/315* (2006.01)

(52) U.S. Cl.
CPC .................. *A61M 5/484* (2013.01); *A61M 5/20* (2013.01); *A61M 5/24* (2013.01); *A61M 5/31551* (2013.01); *A61M 5/31585* (2013.01); *A61M 5/482* (2013.01); *A61M 2005/2026* (2013.01)

(58) Field of Classification Search
CPC A61M 5/24; A61M 5/31551; A61M 5/31585
USPC ................ 604/207–211, 500–506, 232–234, 604/61–64
See application file for complete search history.

(56) References Cited

U.S. PATENT DOCUMENTS

| 5,820,602 | A  | * | 10/1998 | Kovelman et al. | 604/187 |
| 5,961,495 | A  | * | 10/1999 | Walters et al. | 604/208 |
| 7,553,293 | B2 | * | 6/2009  | Jensen et al. | 604/110 |
| 2006/0106362 | A1 | * | 5/2006 | Pass et al. | 604/504 |
| 2006/0173439 | A1 | * | 8/2006 | Thorne et al. | 604/506 |
| 2008/0243087 | A1 |   | 10/2008 | Enggaard | |

FOREIGN PATENT DOCUMENTS

EP 0 338 806 A2 10/1989
WO 2006/045528 A1 5/2006

OTHER PUBLICATIONS

European Search Report Issued in Application No. 09826455.9-1662 dated Oct. 24, 2013.

* cited by examiner

*Primary Examiner* — Kevin C Sirmons
*Assistant Examiner* — Phillip Gray
(74) *Attorney, Agent, or Firm* — Dickinson Wright PLLC

(57) ABSTRACT

An additive force device (111) is connectible with a drug delivery device (100) to increase the amount of force exerted by a user on the dose setting knob (24) to facilitate injection. The additive force device (111) includes a first spring (121) and a loading barrel (135) connected to the first spring (121) for storing torque therein. A ratchet assembly (129) is connected to the loading barrel (135) and to the first spring (121). The ratchet assembly (129) has a first position in which torque is stored in the first spring (121) and a second position in which torque is released from the first spring (121). An inner barrel (133) is connected to the ratchet assembly and to the drug delivery device (100). The inner barrel (133) transmits the stored torque from the first spring (121) to the drug delivery device (100) to increase an injection force thereof.

16 Claims, 17 Drawing Sheets

EXISTING LILLY PEN 1.8 X

| (in)<br>r1 | (lbs)<br>Fin | (lbs)<br>Ft | (in lbs)<br>T=Ft^d | (in)<br>r2 | Fout=T/r2 |
|---|---|---|---|---|---|
| 0.25 | 1 | 0.5 | 0.125 | 0.07 | 1.79 |
| 0.25 | 2 | 1 | 0.25 | 0.07 | 3.67 |
| 0.25 | 4 | 2 | 0.5 | 0.07 | 6.14 |
| 0.25 | 6 | 3 | 0.75 | 0.07 | 10.71 |
| 0.25 | 8 | 4 | 1 | 0.07 | 14.29 |
| 0.25 | 10 | 5 | 1.25 | 0.07 | 17.86 |
| 0.25 | 12 | 6 | 1.5 | 0.07 | 21.73 |
| 0.25 | 14 | 7 | 1.75 | 0.07 | 25.00 |
| 0.25 | 16 | 8 | 2 | 0.07 | 28.87 |
| 0.25 | 18 | 9 | 2.25 | 0.07 | 32.14 |

FIG.12

EXISTING LILLY PEN 1.8 X WITH ADDITIVE TORSION SPRING
(ASSUMES FRICTIONLESS SYSTEM)

| (in) | (lbs) | (lbs) | (in lbs) | | (in) | ADDITIVE TORSION SPRING 1.4in lbs | TOTAL NEW Toque | |
|---|---|---|---|---|---|---|---|---|
| r1 | Fin | Ft | T=Ft^d | | r2 | | T + 1.4 | Fout=T/r2 |
| 0.25 | 1 | 0.5 | 0.125 | | 0.07 | 1.4 | 1.525 | 21.79 |
| 0.25 | 2 | 1 | 0.25 | | 0.07 | 1.4 | 1.65 | 23.57 |
| 0.25 | 4 | 2 | 0.5 | | 0.07 | 1.4 | 1.9 | 27.14 |
| 0.25 | 6 | 3 | 0.75 | | 0.07 | 1.4 | 2.15 | 30.71 |
| 0.25 | 8 | 4 | 1 | | 0.07 | 1.4 | 2.4 | 34.29 |
| 0.25 | 10 | 5 | 1.25 | | 0.07 | 1.4 | 2.65 | 37.86 |
| 0.25 | 12 | 6 | 1.5 | | 0.07 | 1.4 | 2.9 | 41.43 |
| 0.25 | 14 | 7 | 1.75 | | 0.07 | 1.4 | 3.15 | 45.00 |
| 0.25 | 16 | 8 | 2 | | 0.07 | 1.4 | 3.4 | 48.57 |
| 0.25 | 18 | 9 | 2.25 | | 0.07 | 1.4 | 3.65 | 52.14 |
| 0.25 | 20 | 10 | 2.5 | | 0.07 | 1.4 | 3.9 | 55.71 |
| 0.25 | 22 | 11 | 2.75 | | 0.07 | 1.4 | 4.15 | 59.29 |
| 0.25 | 24 | 12 | 3 | | 0.07 | 1.4 | 4.4 | 62.86 |

FIG.13

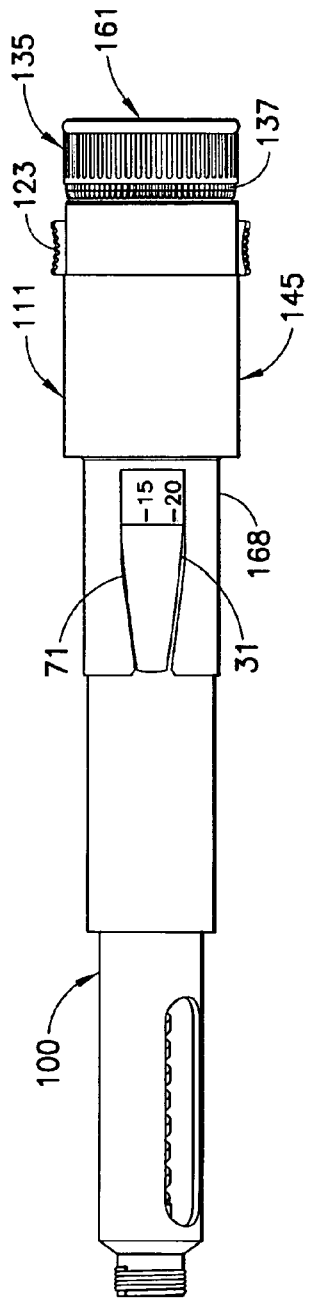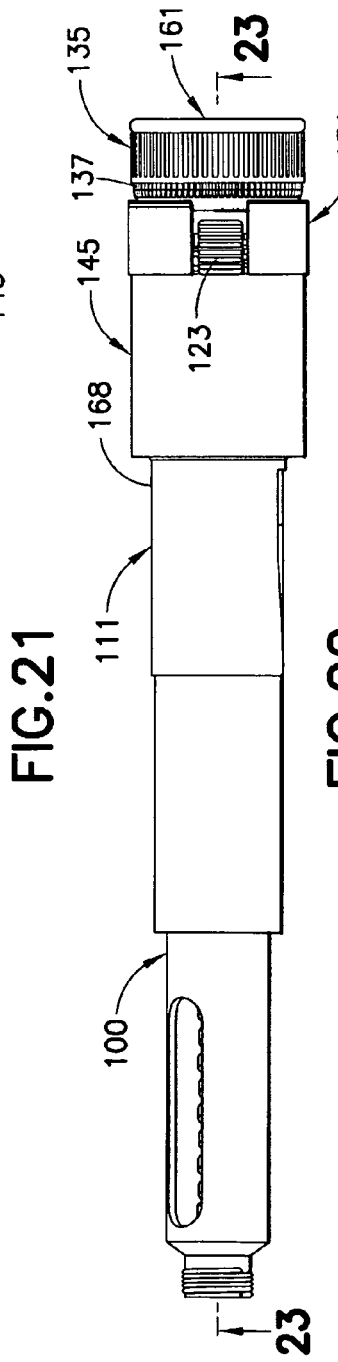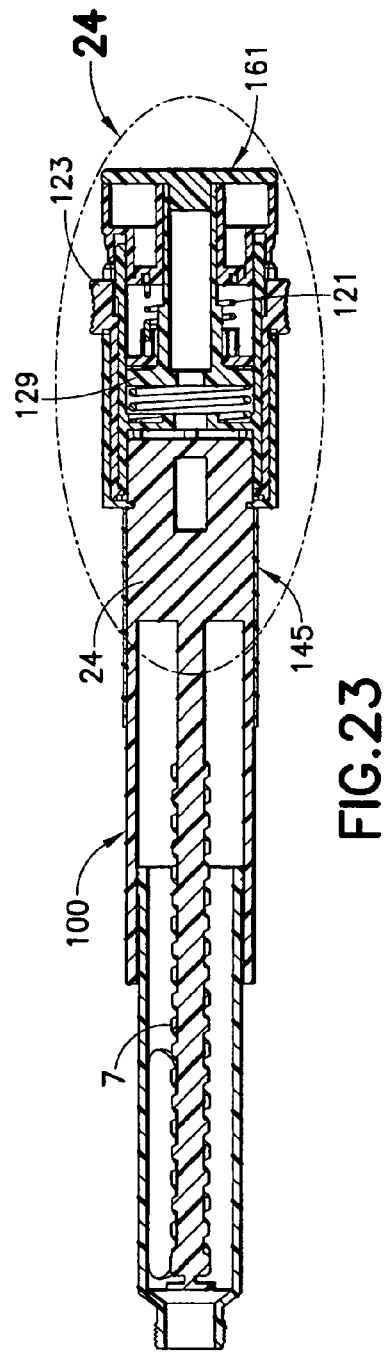

ADDITIVE FORCE DEVICE FOR DRUG DELIVERY PEN FOR INTRADERMAL MEDICATION INJECTION

CROSS REFERENCE TO RELATED APPLICATION

This application claims the benefit under 35 U.S.C. §119 (e) of U.S. Provisional Application Ser. No. 61/193,314, filed Nov. 17, 2008, the entire disclosure of which is hereby incorporated by reference.

FIELD OF THE INVENTION

The present invention relates generally to a drug delivery pen for an intradermal medication injection. More particularly, the present invention generally relates to an additive force device for a drug delivery pen that facilitates intradermal medication injection. Still more particularly, the present invention provides a drug delivery pen having an additive force device that supplies additional injection force to the pen knob of the drug delivery pen to facilitate an intradermal of other high pressure injection of medication.

BACKGROUND OF THE INVENTION

Insulin and other injectable medications are commonly given with drug delivery pens, whereby a disposable pen needle assembly is attached to facilitate drug container access and allow fluid egress from the container through the needle into the patient.

As technology and competition advance, driving the desire for shorter, thinner, less painful, and more efficacious injections, the design of the pen needle assembly and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

The assembly and operation to a typical drug delivery pen, as shown in FIGS. 1 and 2, is described in U.S. Patent Application Publication No. 2006/0229562, published on Oct. 12, 2006 and in U.S. Pat. No. 6,248,095, issued on Jun. 19, 2001, both of which are hereby incorporated by reference in their entirety.

Drug delivery pens, such as the exemplary drug delivery pen 100 shown in FIGS. 1 and 2, are designed for subcutaneous injections and typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 2 is an exploded view of the drug delivery pen 100 of FIG. 1. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

The backpressure in subcutaneous injections is not very large, while the backpressure associated with intradermal injections may be many times greater than that of subcutaneous injections. For example, the backpressure often exceeds 200 psi for an intradermal injection, while the backpressure for a subcutaneous injection is generally in the range of 30-50 psi. Thus, a need exists for a drug delivery pen that has a high mechanical gain to reduce thumb forces required to overcome the initial high breakout force in the cartridge during an intradermal injection.

Existing intradermal drug delivery devices require a large force to inject the medication because of back pressure created from the intradermal layer, thereby making the intradermal injection difficult. Therefore, a need exists for a drug delivery pen that has an additive force device to add to the user's input force of depressing the injection button to allow an intradermal injection to be made with a low user force.

Accordingly, a need exists for a drug delivery pen that facilitates intradermal medication injection.

SUMMARY OF THE INVENTION

In accordance with an aspect of the present invention, an additive force device for drug delivery is provided that supplies additional force during an injection by adding force to the user's force, thereby facilitating the intradermal medication injection.

The additive force device includes an energy storage device, such as a torsion spring or a compression spring, used with a drug delivery pen, or other similar device, to aid a user during an injection by supplying additional force to a plunger of the drug delivery pen. Preferably, the additional force is supplied when a preset force is exceeded. The additive force device is loaded with a twist of a barrel, and then the dose is set on the drug delivery pen. The drug delivery pen is then used in its normal manner. When the force exerted by the user rises above a predetermined value, for example, five pounds or any other suitable ergonomic value, a mechanism releases the energy stored in the energy storage device to turn the pen's mechanism to effectively add force to the force exerted by the user.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIG. 12 is a table of the user input force and the resulting output force generated by a conventional drug delivery pen;

FIG. 13 is a table of the user input force and the resulting output force generated by a drug delivery pen to which an additive force device according to an exemplary embodiment of the present invention has been connected;

FIGS. 21 and 22 are side elevational views of the additive force device connected to a drug delivery pen of FIGS. 17 and 18;

FIG. 23 is a side elevational view in cross section of the additive force device and drug delivery pen of FIG. 22;

Throughout the drawings, like reference numbers will be understood to refer to like parts, components and structures.

DETAILED DESCRIPTION OF THE EXEMPLARY EMBODIMENTS

Figure 1:
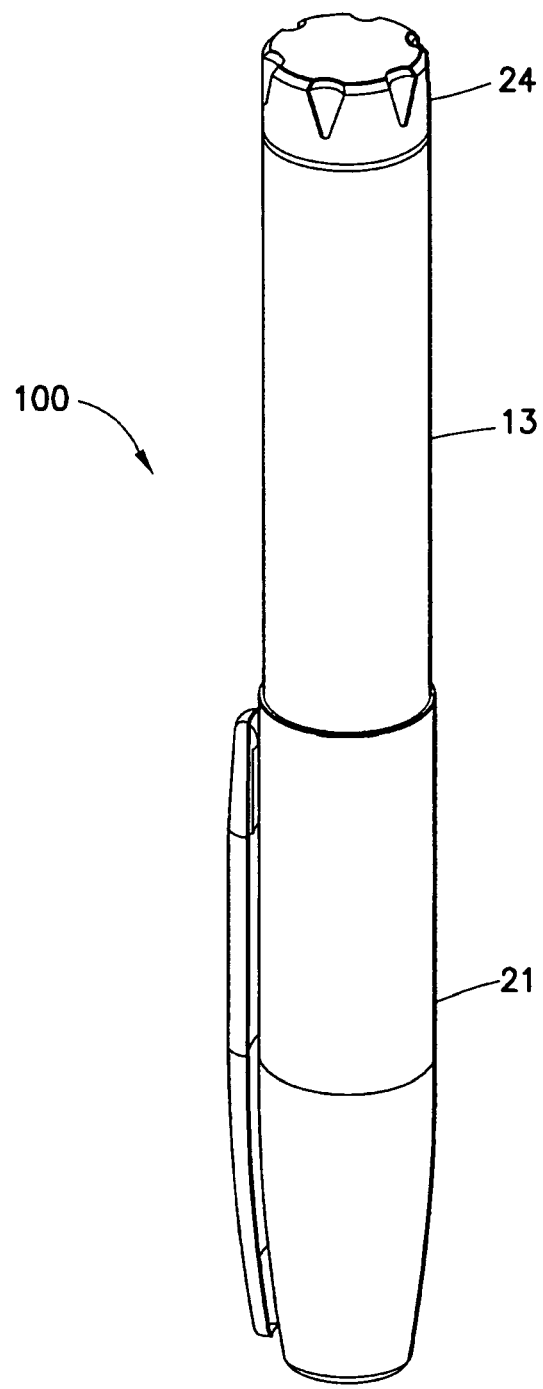
FIG. 1 is a perspective view of an assembled drug delivery pen.
Figure 2:
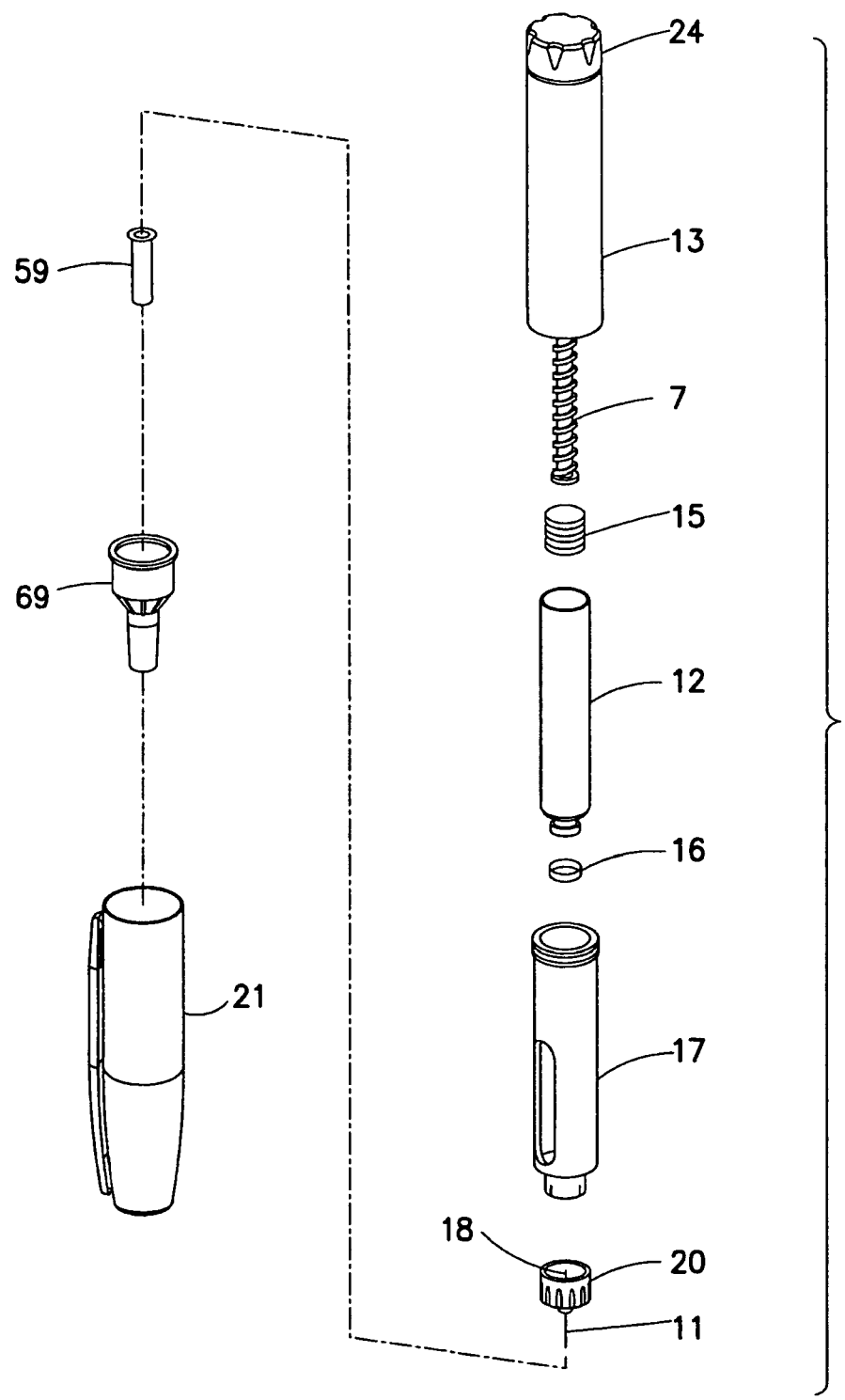
FIG. 2 is an exploded perspective view of the components of the drug delivery pen of FIG. 1.
Figure 3:
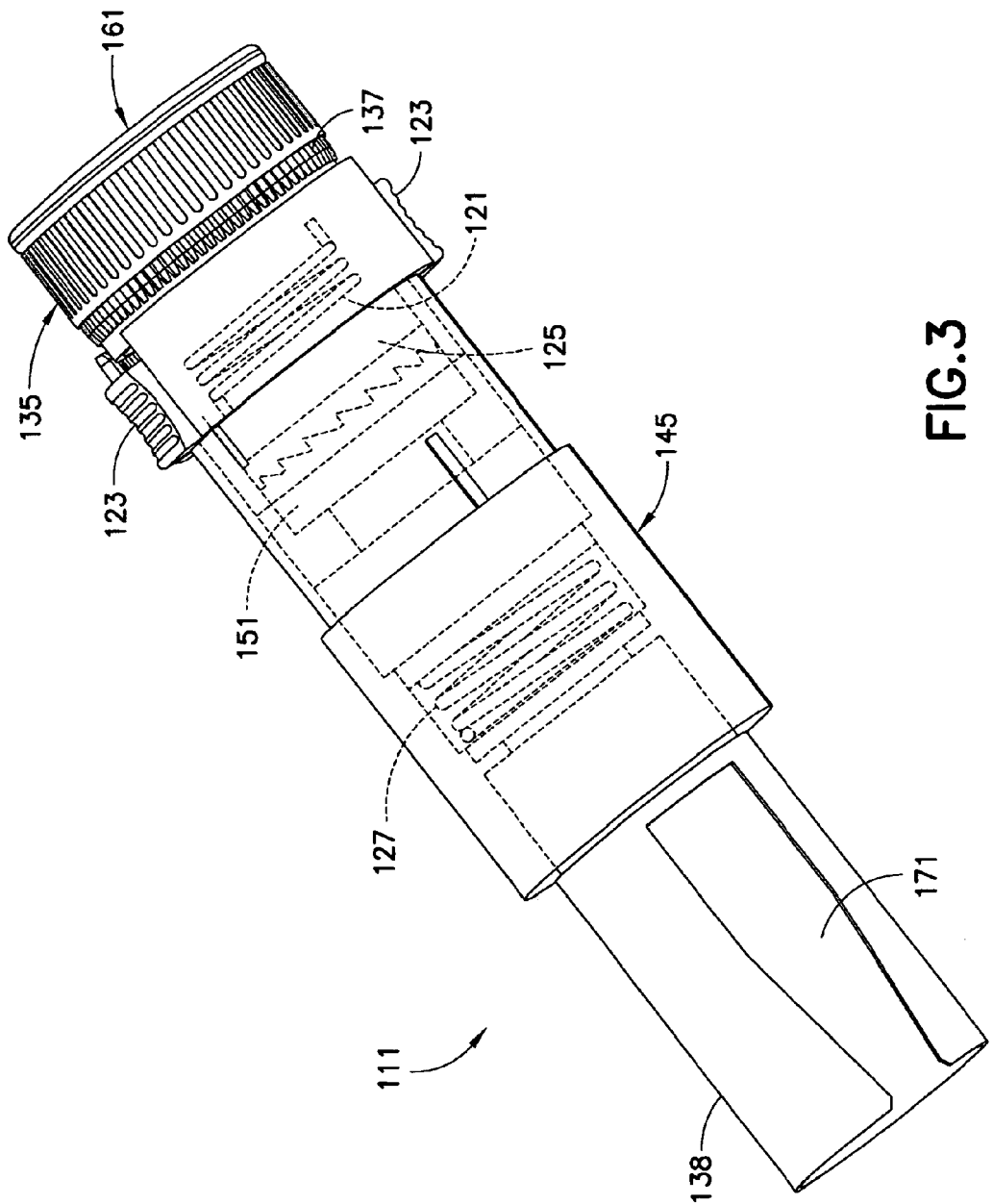
FIG. 3 is a perspective view in cross section of an additive force device for a drug delivery pen for intradermal medication injection.

The following description and details of exemplary embodiments of the present invention are disclosed with reference to a typical drug delivery pen 100, as shown in FIGS. 1 and 2. However, the additive force device of the present invention may be used with any suitable drug delivery pen. The pen may be provided with a subcutaneous patient needle 11 as shown or with a shorter (approximately between 0.5-3 mm and preferably approximately between 1.5-2 mm) intradermal patient needle.

In the exemplary embodiment of the present invention shown in FIGS. 3-25, the additive force device 111 is connected to an existing drug delivery pen 100 (FIGS. 1 and 2), as shown in FIGS. 17-25. An additive force device 111 is connectible with a drug delivery pen 100 to increase the amount of force exerted by a user on the pen knob 24 to facilitate injection. The additive force device 111 includes a first spring 121 and a loading barrel 135 connected to the first spring 121 for storing torque therein. A ratchet assembly 129 is connected to the loading barrel 135 and to the first spring 121. The ratchet assembly has a first position in which torque is stored in the first spring 121 and a second position in which torque is released from the first spring 121. An inner barrel 133 is connected to the ratchet assembly and to the drug delivery pen 100. The inner barrel 133 transmits the stored torque from the first spring 121 to the drug delivery pen 100 to increase an injection force thereof.

The additive force device 111 includes a button 161 connected to a loading barrel 135. A lower ratchet 151 is connected to the loading barrel 135. An upper ratchet 125 is connected to the lower ratchet 151. A first spring 121 is disposed between the loading barrel 135 and the upper ratchet 125. The upper ratchet 125 is connected to an inner barrel 133. A second spring 127 is disposed between the inner barrel 133 and the lower ratchet 151. An outer barrel 131 is connected to the inner barrel 133 and to the knob 24 of the drug delivery pen 100. A fixing barrel 145 is connected to the outer barrel 131 and to the drug delivery pen 100.

Figure 19:
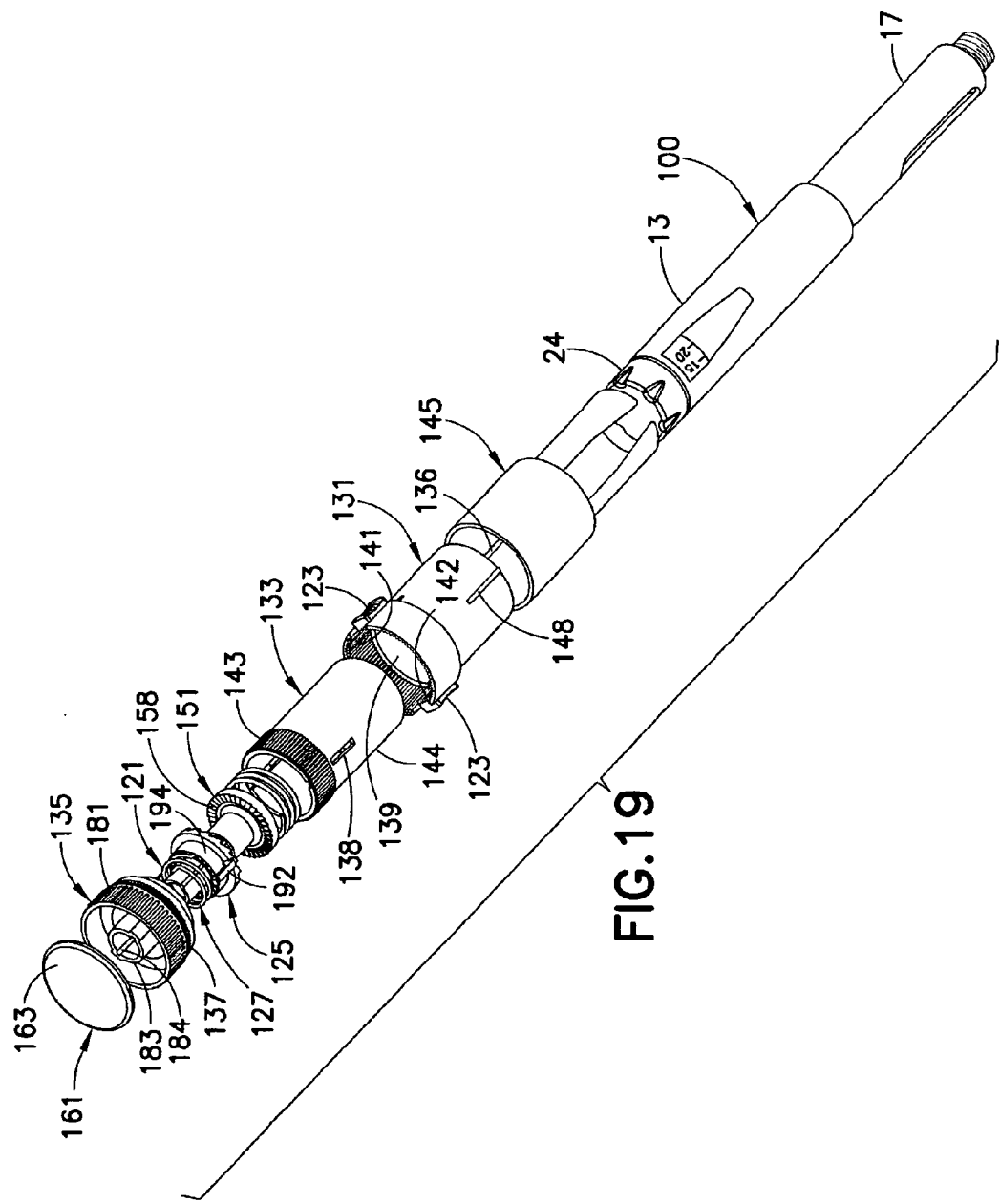
FIGS. 19 and 20 are exploded perspective views of the additive force device and drug delivery pen of FIGS. 17 and 18.
Figure 20:
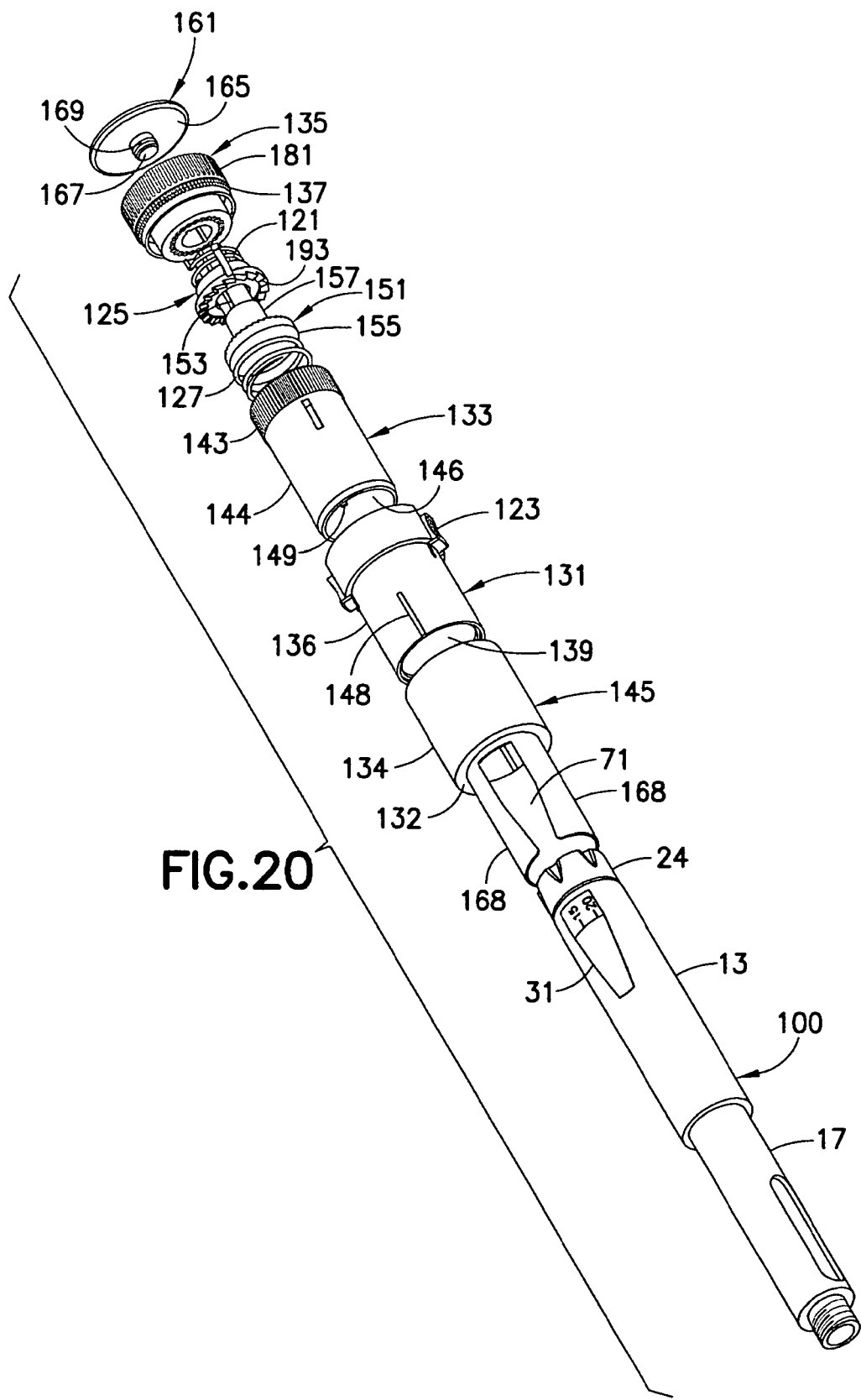

The button 161 has a substantially planar outer surface 163, as shown in FIG. 19. A protrusion 167 extends outwardly from an inner surface 165. A circumferential rib 169 extends around the protrusion, as shown in FIG. 20. The circumferential rib 169 facilitates securing the button 161 to the lower ratchet 151.

The loading barrel 135 has an inner wall 181 and an outer wall 183. A groove 184 extends axially along an inner surface of the inner wall 181 and receives the rib 153 of the lower ratchet 151, thereby keying the loading barrel 135 to the lower ratchet 151. Preferably, a second groove is disposed diametrically opposite the first groove 184 to receive the second rib of the lower ratchet 151.

The ratchet assembly 129 includes a lower ratchet 151 and an upper ratchet 125. The lower ratchet 151 has a base 155 and a shaft 157 extending outwardly therefrom. A rib 153 extends axially along an outer surface of the shaft 157. Preferably, a second rib is diametrically opposed to the rib 153. A plurality of teeth 158 are disposed on an upper surface of the base 155.

Figure 4:
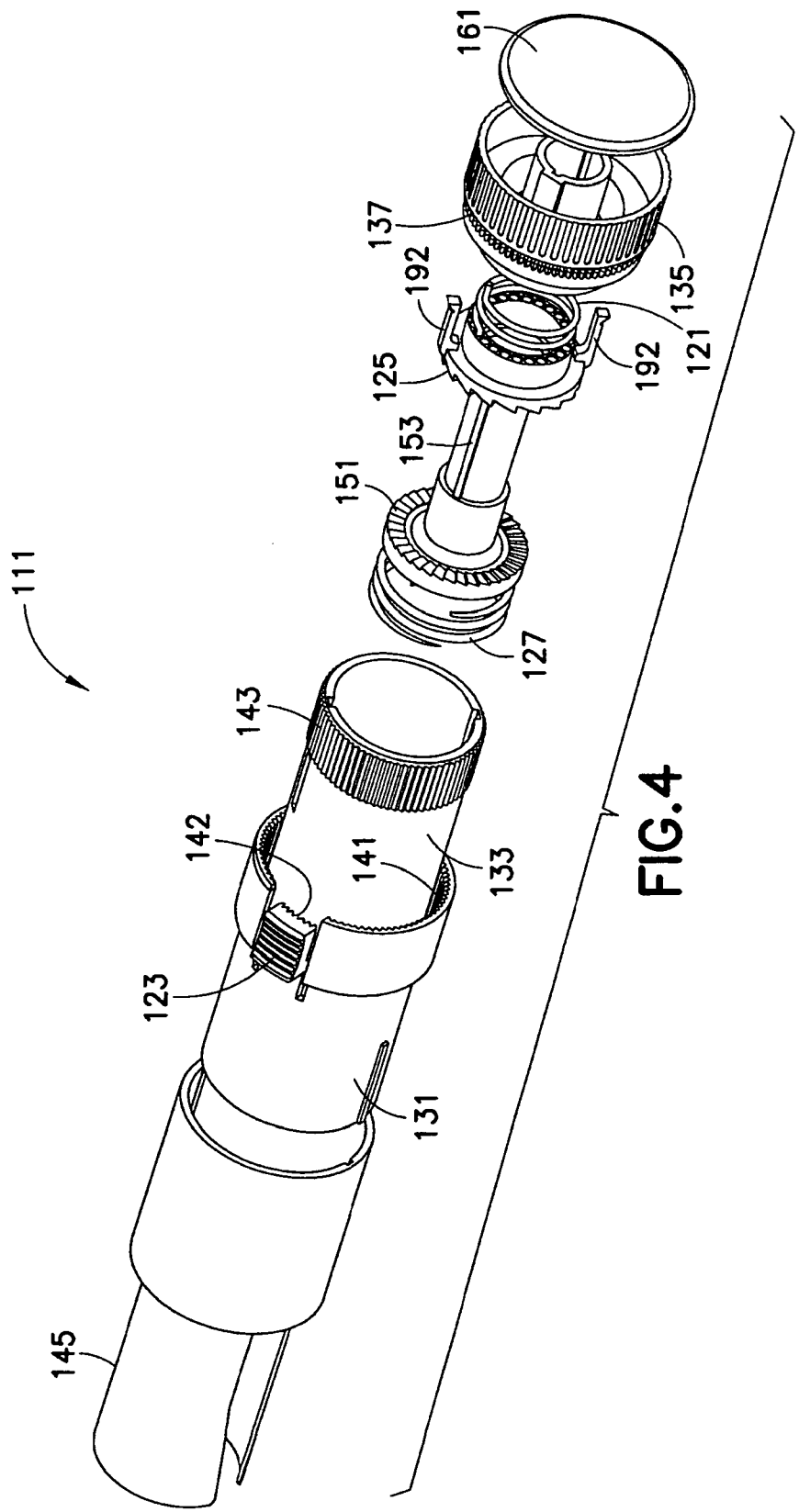
FIG. 4 is an exploded perspective view of the additive force device of FIG. 3.
Figure 7:
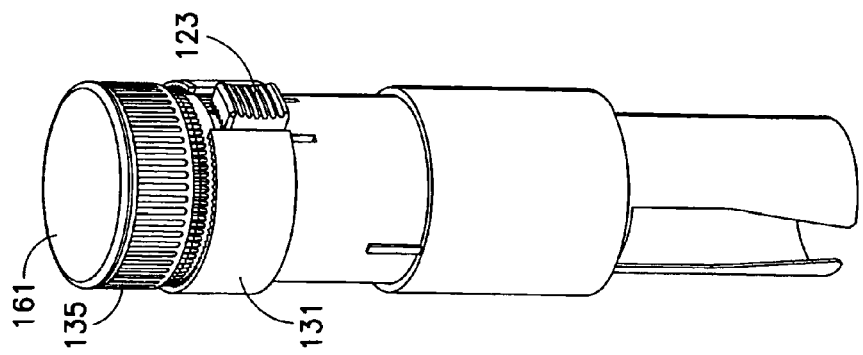
FIG. 7 is a perspective view of the additive force device of FIG. 5.
Figure 6:
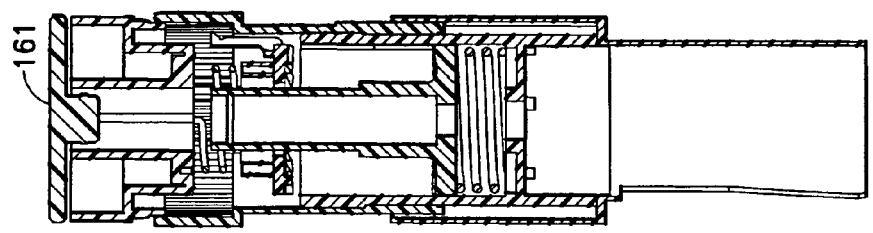
FIG. 6 is a front elevational view in partial cross section of the additive force device of FIG. 5.
Figure 5:
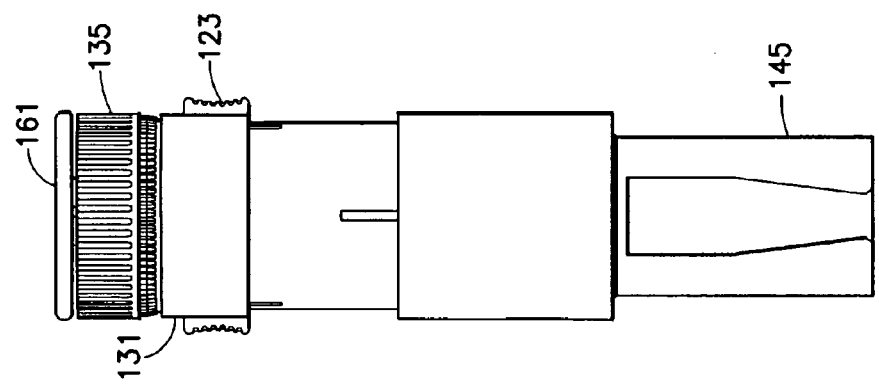
FIG. 5 is a front elevational view of the additive force device of FIG. 3 prior to a dose being set.
Figure 8:
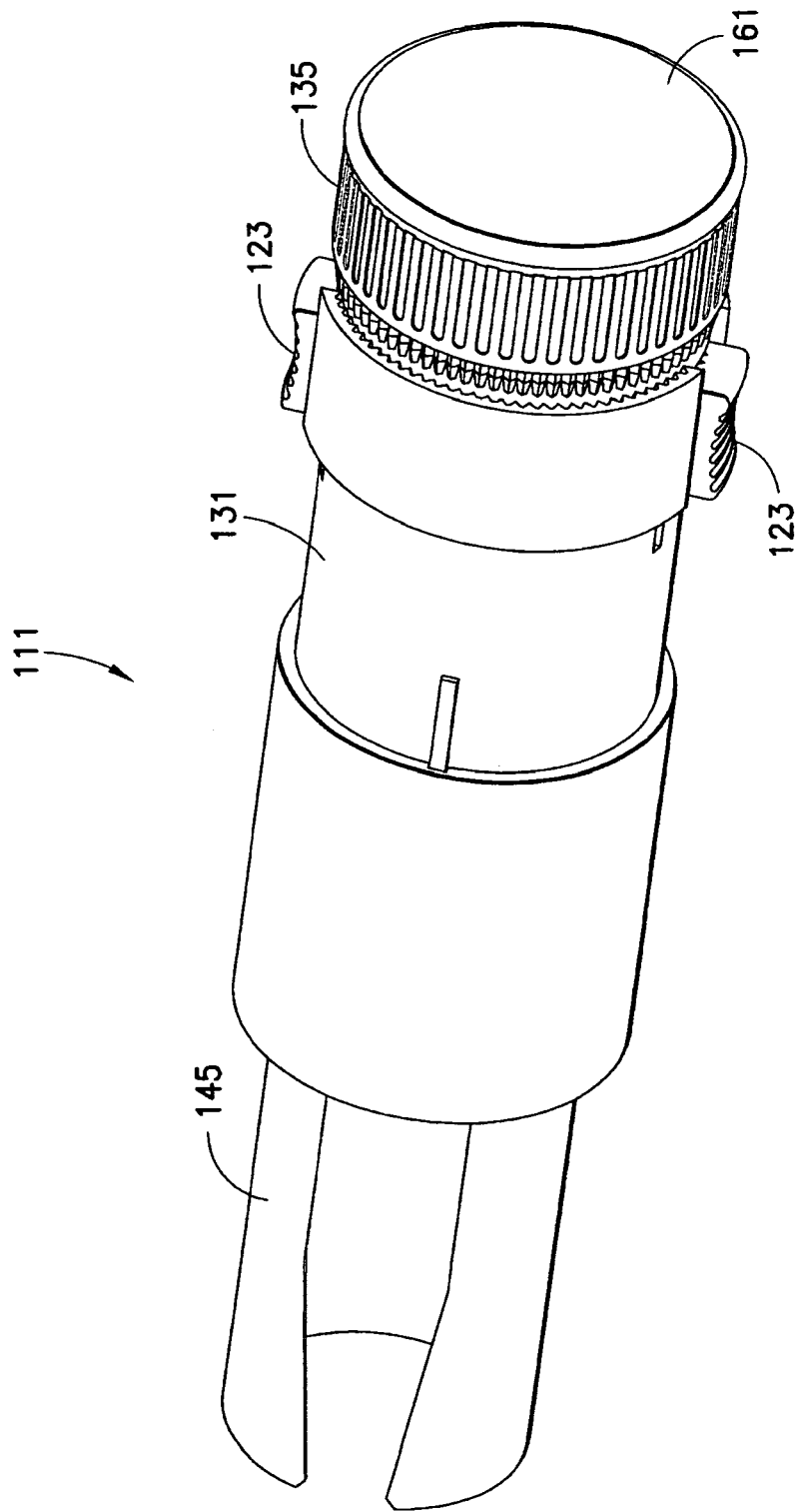
FIG. 8 is a perspective view of the additive force device of FIG. 3 after a dose has been set.
Figure 9:
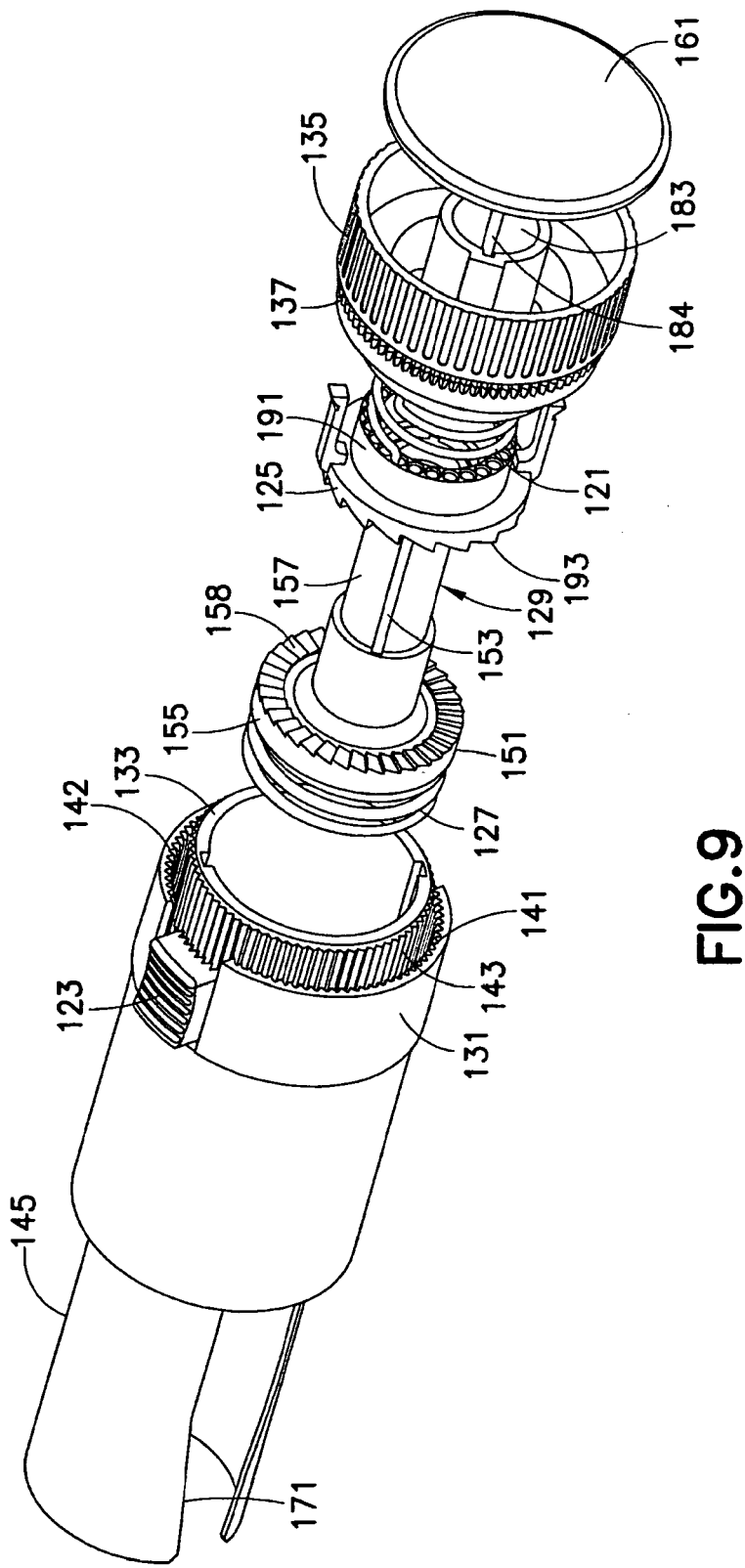
FIG. 9 is an exploded perspective view of the additive force device of FIG. 3.
Figure 11:
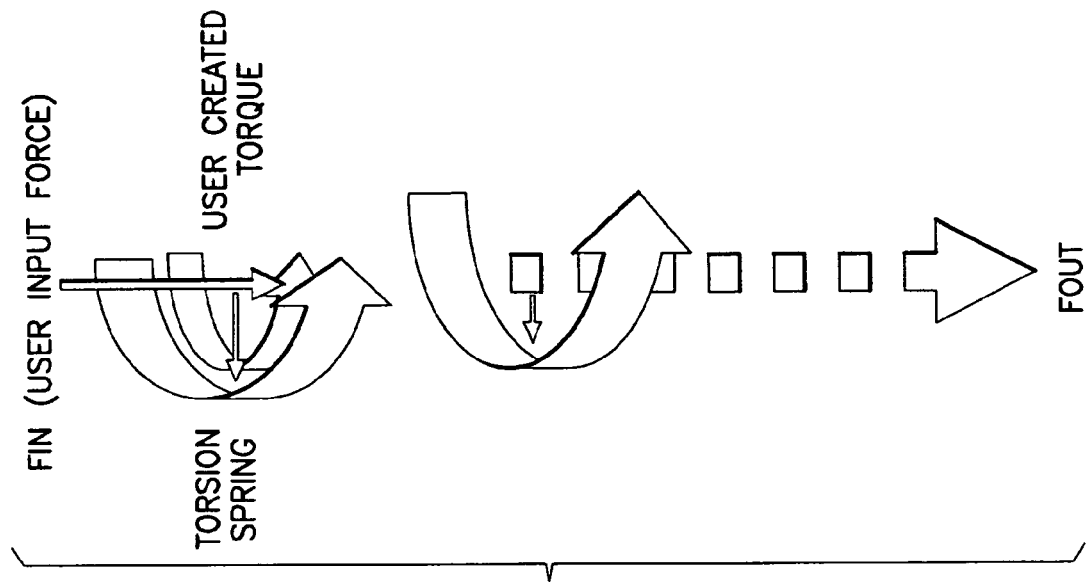
FIG. 11 is an illustration of the force input by a user and the resulting output force generated by a drug delivery pen to which an additive force device according to an exemplary embodiment of the present invention has been connected.
Figure 10:
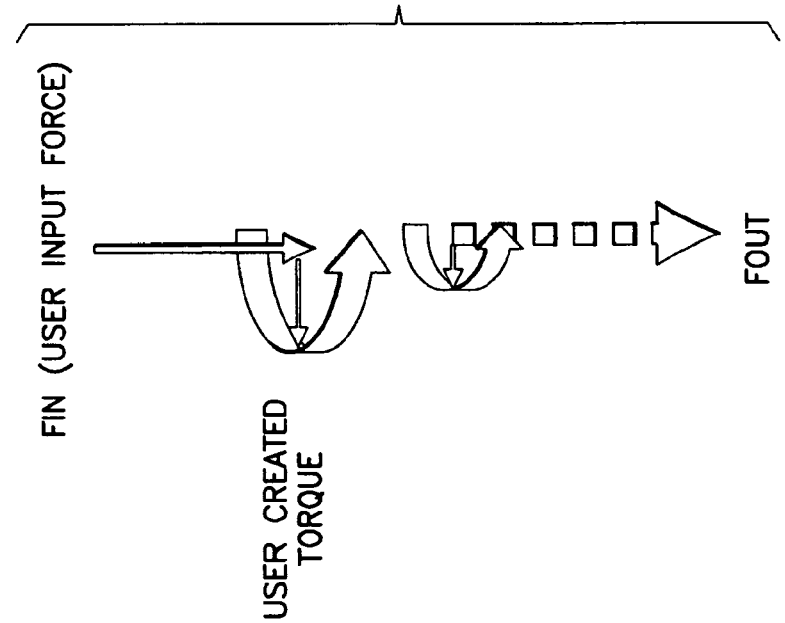
FIG. 10 is an illustration of the force input by a user and the resulting output force generated by a conventional drug delivery pen.

The upper ratchet 125 has a base 191. A plurality of teeth 193 are disposed on a lower surface of the base 191. The plurality of teeth 193 of the upper ratchet 125 are adapted to engage the plurality of teeth 158 of the lower ratchet 151. An arm 192 extends upwardly from the base 191. Preferably, a second arm 192 is disposed diametrically opposite the first arm 192, as shown in FIG. 4. The arm 192 keys the upper ratchet 125 to the inner barrel 133. A wall 194 extends upwardly from the base 191 of the upper ratchet 125.

Figure 24:
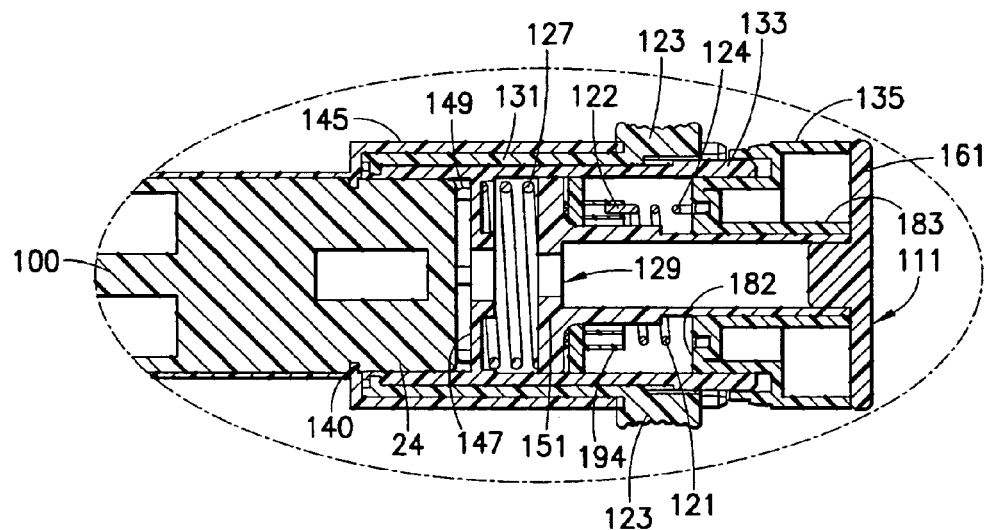
FIG. 24 is an enlarged elevational view in cross section of the additive force device of FIG. 23.

A first spring 121 is disposed between the upper ratchet 125 and the loading barrel 135. A first end 122 of the first spring 121 is secured to the wall 194 of the upper ratchet 125, as shown in FIG. 24. A second end 124 of the first spring 121 is received by a surface 182 of the loading barrel 135. Preferably, the first spring 121 is a torsion spring, although any suitable spring may be used.

Figure 25:
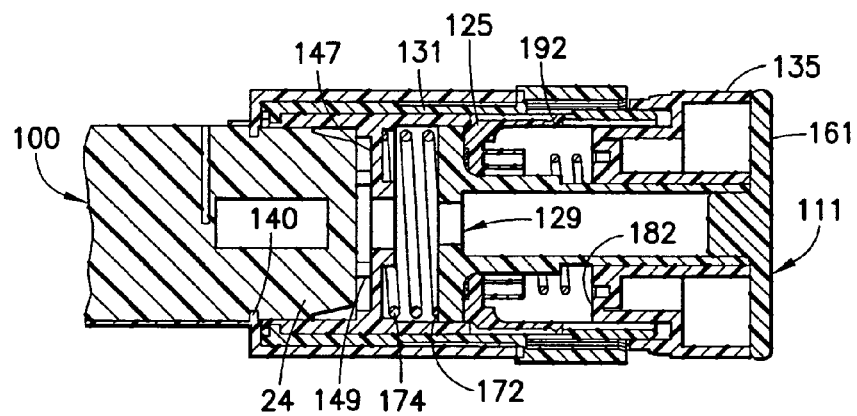
FIG. 25 is an enlarged elevational view in cross section in which the additive force device of FIG. 24 is rotated approximately 90 degrees.

An inner barrel 133 preferably has a substantially cylindrical shape and has an outer surface 144 and an inner surface 146, as shown in FIGS. 19 and 20. Splines extend axially along a portion of the outer surface 146 of the inner barrel 133. A base 147 is disposed within the inner barrel 133, as shown in FIGS. 24 and 25. A plurality of notches 149 are disposed on the inner surface 146 of the inner barrel and are adapted to key the inner barrel to corresponding notches 25 (FIG. 1) of the pen knob 24 of the drug delivery pen 100.

A second spring 127 is disposed between the lower ratchet 151 and the inner barrel 133, as shown in FIGS. 24 and 25. A first end 172 of the second spring 127 engages the lower ratchet 151. A second end 174 of the second spring 127 is received by the base 147 of the inner barrel 133. Preferably, the second spring 127 is a compression spring, although any suitable spring may be used. The second spring 127 biases the lower ratchet 151 toward the upper ratchet 125 such that the teeth of the lower ratchet engage the teeth of the upper ratchet.

An outer barrel 131 has a preferably substantially cylindrical shape and has an outer surface 136 and an inner surface 138, as shown in FIGS. 19 and 20. Flexible buttons 123 are movably formed in the outer barrel 131. A rib 148 extends axially along an outer surface 136 of the outer barrel 131. Preferably, a second rib is disposed diametrically opposite the first rib 148.

A fixing barrel 145 has a base 132, as shown in FIG. 20. A wall 134 extends upwardly from the base 132. A groove 136 extends axially along an inner surface of the wall 134. Preferably, a second groove is disposed diametrically opposite the first groove 136. The groove 136 receives the rib 148 of the outer barrel, thereby keying the outer barrel to the fixing barrel 145. A pair of flexible legs 138 extends downwardly from the base and are adapted to secure the additive force device 111 to the drug delivery pen. Preferably, a window 171 is formed between the flexible legs 138 such that a dose setting window 31 of the drug delivery pen 100 is visible to a user after the additive force device 111 is connected to the drug delivery pen 100, as shown in FIG. 21.

Assembly and Operation

Energy is stored in an energy storage device, such as a torsion spring or a compression spring. The inner barrel 133 is attached to the pen knob 24 of the drug delivery pen 100 to transmit torque generated by the additive force device 111 to the drug delivery pen 100. Preferably, the inner barrel 133 is rigidly keyed to the outer sleeve 13 of the drug delivery pen 100. The outer sleeve 13 of the drug delivery pen 100 is preventing from rotating while torquing the barrel 135 of the force additive device 111 and storing energy (torque) in the torsion spring 121 by the engagement of the splines of the buttons 123 and the inner barrel 133. The torsion spring energy is held by a one-way ratchet system that is held together by the second spring 127. The fixing barrel 145 is attached to the outer sleeve 13 of the drug delivery pen 100 in any suitable manner, such as by a snap connect or friction fit. As shown in FIGS. 24 and 25, inwardly extending tabs 140 of the fixing barrel 145 may secure the fixing barrel to the drug delivery pen 100 by a snap connect.

Figure 14:
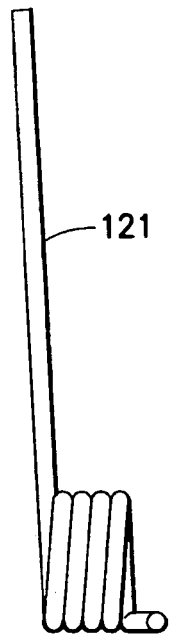
FIGS. 14-16 are side and front elevational views and a perspective view of a torsion spring.
Figure 16:
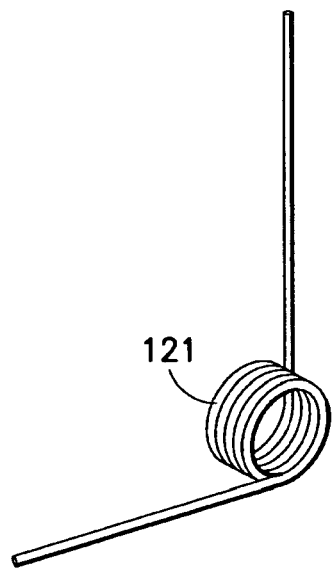
Figure 15:
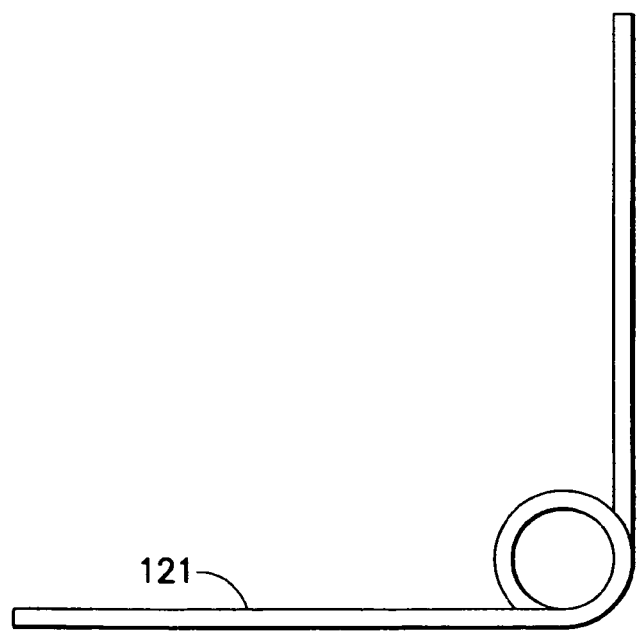
Figure 17:
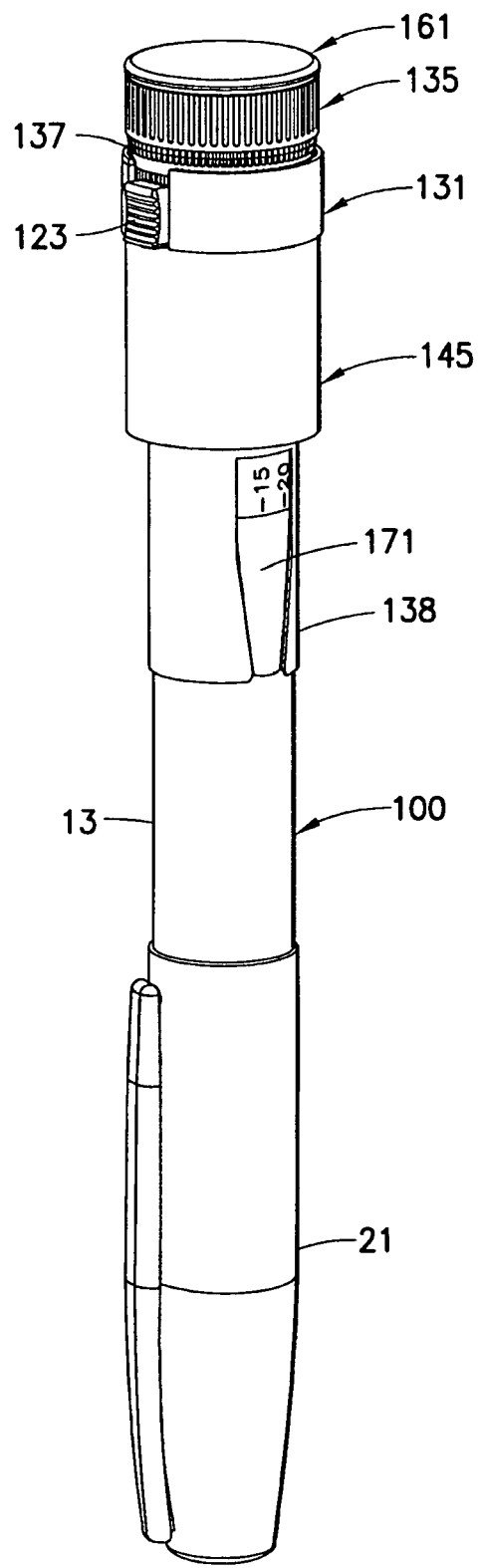
FIGS. 17 and 18 are elevational views of a additive force device of FIG. 3 connected to a drug delivery pen.
Figure 18:
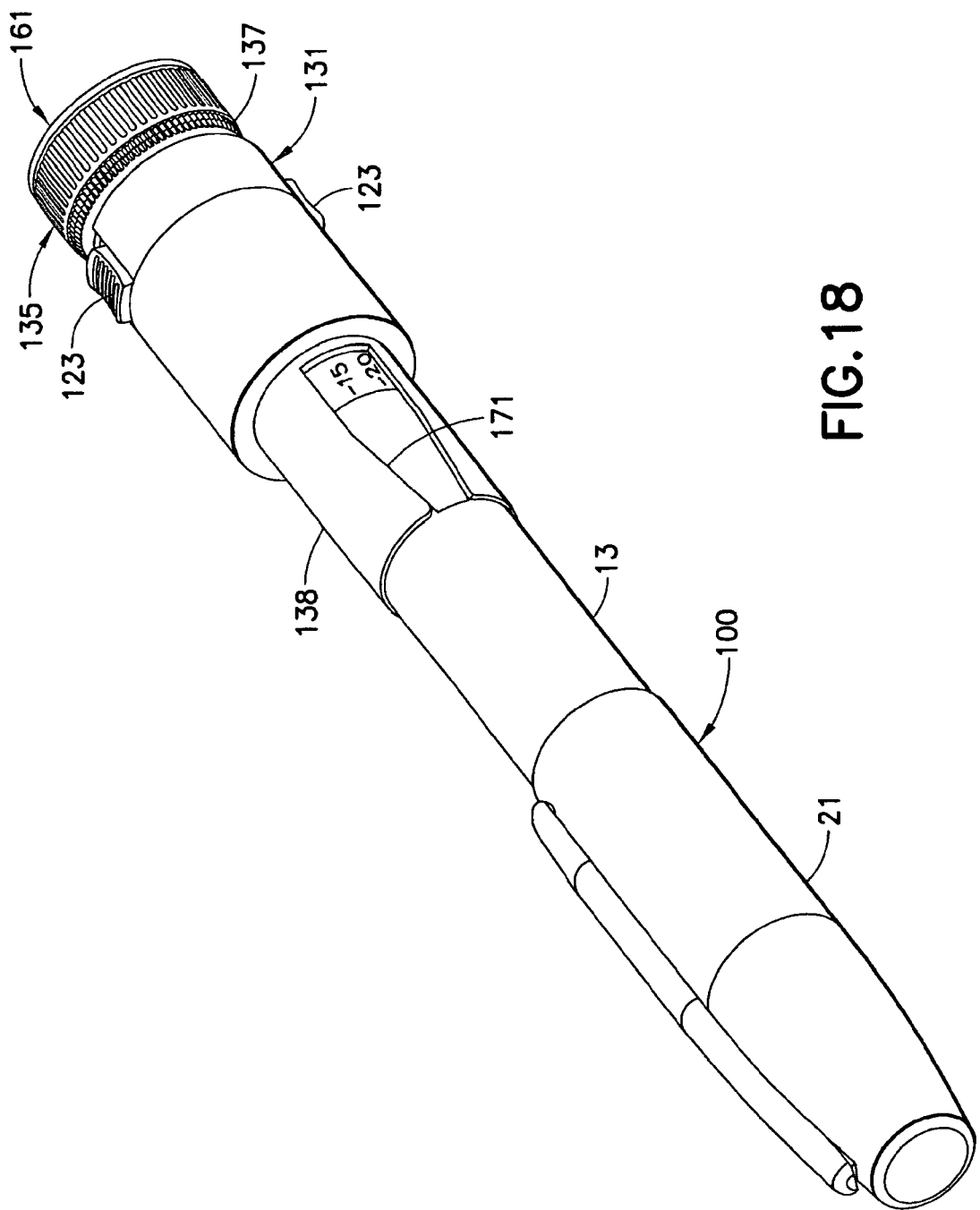

Although not limited thereto, the following description refers to the first spring 121 being a 1.4 in-lbs torsion spring 121 as shown in FIGS. 14-16. The first spring 121 may be loaded before or after connecting the additive force device 111 to the drug delivery pen 100 by twisting the loading barrel 135 while pressing the cantilever buttons 123. As the user grasps the loading barrel 135 and the buttons 123 are being flexed inwardly, the splines 142 of the outer barrel 131 engage the corresponding splines 143 of the inner barrel 133 to prevent the inner barrel 133 from rotating as the loading barrel 135 is rotated to load the torsion spring 121. The loading barrel 135 is keyed to the lower ratchet 151 by the groove 184 and rib 153. The compression spring 127 applies a constant biasing force on the lower ratchet 151 to contact the lower ratchet 151 with the upper ratchet 125 such that the teeth of the upper and lower ratchets engage. The upper ratchet 125 is keyed to the inner barrel 133 by the arms 192 engaging openings 138 in the inner barrel. By depressing the buttons 123, the splines of the outer barrel 133 and the inner barrel 131 engage such that the inner barrel is prevented from rotating when the loading barrel 135 is rotated. The plurality of teeth of the upper ratchet 125 slide over the plurality of teeth of the lower ratchet 151, thereby creating an audible indication that the first spring is being energized.

After the additive force device 111 is connected to the drug delivery pen 100, the dose is set using the additive force device. The user grasps and rotates the loading barrel 135 to set the desired dose. The window 171 formed in the fixing barrel 145 allows the user to view the dose setting window 31 of the drug delivery pen. The fingers 123 are not flexed inwardly such that the pen knob 24 rotates with rotation of the loading barrel 135, thereby allowing the user to set the dose.

The loading barrel 135 is keyed to the lower ratchet 151 such that the lower ratchet rotates with the loading barrel. The plurality of teeth 158 of the lower ratchet 151 engage the plurality of teeth 193 of the upper ratchet 125 because the second spring 127 biases the lower ratchet against the upper ratchet. The upper ratchet 125 is keyed to the inner barrel 133 by the arms 192 engaging the inner barrel, as shown in FIG. 25. The inner barrel 133 is keyed to the pen knob 24 such that rotation of the loading barrel 135 results in rotation of the pen knob 24. Accordingly, the rotation of the pen knob 24 moves the pen knob away from the outer sleeve 13 of the drug delivery pen 100 as with normal operation of the drug delivery pen.

Outward movement of the pen knob 24 causes the pen knob to push the base 147 of the inner barrel 133 toward the button 161. The outer barrel 131 is keyed to the fixing barrel 145 by the rib 148 and groove 136, such that the outer barrel 131 moves axially relative to the fixing barrel 145. Accordingly, when the pen knob 24 moves outwardly, the resulting movement of the inner barrel 133 moves the outer barrel 131 along the axial groove 136 of the fixing barrel 145. The inner barrel 133 also pushes the second spring 127, which pushed the lower ratchet 151 and upper ratchet 125 as well as the loading barrel 135 outwardly. An injection may now be made with the drug delivery pen 100.

To make an injection, the user pushes the button 161 of the additive force device 111 toward the drug delivery pen 100. The inner surface 165 of the button 161 contacts the loading barrel 135 such that the loading barrel moves with the button 161. Inward movement of the loading barrel 135 pushes the lower ratchet 151, which is keyed to the loading barrel, inwardly. The lower ratchet 151 and the upper ratchet 125 remain engaged such that rotation of the upper ratchet 125 is prevented and the energy stored in the first spring 121 is not released. The lower ratchet 151 pushes the compression spring 127, which in turn pushes on the base 147 of the inner barrel 133. Inward movement of the inner barrel 133 results in inward movement of the pen knob 24, which is keyed to the inner barrel 133, thereby administering medicament in accordance with normal operation of the drug delivery pen 100.

When the force required to administer the medicament is greater than a predetermined preload, five pounds for example, the second spring 127 compresses such that the lower ratchet 151 is disengaged from the upper ratchet 125. When the plurality of teeth 158 of the lower ratchet 151 disengage from the plurality of teeth 193 of the upper ratchet 125, the upper ratchet 125 is free to rotate. The energy stored in the first spring 121 is released and causes the upper ratchet 125 to rotate. The rotation of the upper ratchet 125 causes rotation of the inner barrel 133, which is keyed to the upper ratchet 125. The rotation of the inner barrel 133 rotates the pen knob 24 because the pen knob 24 is keyed to the inner barrel. Accordingly, the torque stored in the first spring 121 is transmitted to the pen knob 24, thereby adding to the user input force. The medicament is administered with the drug delivery pen in accordance with normal operation thereof.

The second end 124 of the first spring 121 is connected to the loading barrel 135. The inward movement of the loading barrel 135 (resulting from the button 161 being pushed inwardly) causes the splines 137 of the loading barrel 135 to engage the splines 141 of the outer barrel 131. The splines 137 of the loading barrel 135 and the splines 141 of the outer barrel 131 are initially spaced apart by the second spring 127. The splines 137 of the loading barrel 135 and the splines 141 of the outer barrel 131 engage when a user feels a high injection force. The outer barrel 131 is keyed to the fixing barrel 145, which is in turn keyed to the drug delivery pen 100. Accordingly, the loading barrel 135 is prevented from rotating such that the torque is delivered to the upper ratchet 125.

The torsion supplied is translated to a linear force by the drug delivery pen's own mechanism and assists the user by supplying force over and above the user's finger applied force, thereby allowing the user to accomplish a more difficult intradermal medication injection.

The force additive device 111 according to exemplary embodiments of the present invention adds force to aid the user during injection preferably when the user experiences a high injection force. When the user does not experience a high force, the force additive device 111 is not activated and remains cocked until additional force is required. Some users may not require the additional force, but the force additive device 111 remains cocked should a high injection force be experienced. No action is necessary when the force additive device 111 remains cocked.

The force additive device 111 applies force to aid the user at the moment when the user experiences the high injection force and not before such time. Thus, the stored energy of the first spring 121 is applied when it is needed most and preferably only at such time. This configuration optimally utilizes the torque stored in the first spring 121 by applying the maximum amount of the stored energy to the highest pressure peak recorded on an intradermal pressure graph.

A color indicator window may be added to visually alert the user when the device is cocked. For example, the color green may be used to indicate that the force additive device is cocked and the color red to indicate that the force additive device needs to be cocked.

As shown in FIGS. 12 and 13, input forces and respective output forces are shown for a drug delivery pen with (FIG. 13) and without (FIG. 12) the force additive device. For example, a drug delivery pen without the force additive device outputs 7.14 pounds for a four pound input, as shown in FIG. 12. An output of approximately twenty pounds is required to overcome the intradermal back pressure. Adding a 1.4 in lb torque to the pen barrel using the torsion spring of FIGS. 14-16 adds output force to the drug delivery pen. As shown in FIG. 13, a 27.14 lb force is output when four pounds is input to a drug delivery pen 100 including the force additive device 111 such that the user input force of approximately 4 lb is sufficient to overcome intradermal back pressure. The results of FIGS. 12 and 13 are diagrammatically illustrated in FIGS. 10 and 11, respectively.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. An additive force device for use with a drug delivery device, comprising:
    a first spring comprising a torsion spring and having a first end;
    a loading barrel connected to said first spring for storing torque therein;
    a ratchet assembly connected to said loading barrel and wherein said first spring is secured to said loading barrel, said ratchet assembly having a first position in which torque is stored in said first spring and a second position in which torque is released from said first spring; and
    an inner barrel connected to said ratchet assembly and to the drug delivery device, said inner barrel transmitting the stored torque from said first spring to the drug delivery device to increase an injection force thereof, wherein said ratchet assembly includes a lower ratchet and an upper ratchet, each of said lower and upper ratchets having a plurality of teeth for engagement therebetween.

2. The additive force device for use with a drug delivery device of claim 1, wherein
    said lower ratchet is connected to said loading barrel.

3. The additive force device for use with a drug delivery device of claim 2, wherein
    said upper ratchet is connected to said first spring.

4. The additive force device for use with a drug delivery device of claim 3, wherein
    a second spring is disposed between said inner barrel and said lower ratchet to bias said lower ratchet against said upper ratchet.

5. The additive force device for use with a drug delivery device of claim 4, wherein
    said lower and upper ratchets are engaged when said ratchet assembly is in said first position, and said lower and upper ratchets are spaced apart when said ratchet assembly is in said second position.

6. The additive force device for use with a drug delivery device of claim 5, wherein
    said inner barrel is disposed in an outer barrel, said outer barrel having a flexible button for engaging said inner barrel when torque is being supplied to said first spring to substantially prevent movement of said inner barrel and said lower ratchet.

7. The additive force device for use with a drug delivery device of claim 1, wherein
    said second spring comprises a compression spring.

8. The additive force device for use with a drug delivery device of claim 7, wherein
    said second spring has a preload of approximately five pounds.

9. The additive force device for use with a drug delivery device of claim 6, wherein a fixing barrel is connected to said outer barrel and to said drug delivery device, said outer barrel being axially movable within said fixing barrel.

10. The additive force device for use with a drug delivery device of claim 9, wherein
said loading barrel being engaged with said outer barrel when said ratchet assembly is in said second position to substantially prevent movement of said loading barrel.

11. A medicament delivery device, comprising:
a drug delivery pen having a dose setting knob at an end thereof; and
an additive force device connected to said dose setting knob end of said drug delivery pen, said additive force device including
a firsts comprising a torsion spring;
a loading barrel connected to said first spring for storing torque therein;
a lower ratchet connected to said loading barrel;
an upper ratchet connected to said lower ratchet and to said first spring, each of said lower and upper ratchets having a plurality of teeth for engagement therebetween; and
an inner barrel connected to said upper ratchet and to the drug delivery pen,
wherein torque is stored in said first spring, when said upper and lower ratchets are engaged torque is prevented from being released from said first spring, and when said upper and lower ratchets are separated said inner barrel transmits the stored torque from said first spring to the drug delivery pen to increase an injection force thereof.

12. The medicament delivery device of claim 11, wherein
a second spring is disposed between said inner barrel and said lower ratchet to bias said lower ratchet against said upper ratchet.

13. The medicament delivery device of claim 11, wherein
said inner barrel is disposed in an outer barrel, said outer barrel having a flexible button for engaging said inner barrel when torque is being supplied to said first spring to substantially prevent movement of said inner barrel and said lower ratchet.

14. An additive force device for use with a drug delivery device, comprising:
a first spring comprising a torsion spring and having a first end and a second end;
a loading barrel having a surface receiving said first spring for storing torque therein;
a ratchet assembly connected to said loading barrel and to said first spring, said ratchet assembly having a first position in which torque is stored in said first spring and a second position in which torque is released from said first spring; and
an inner barrel connected to said ratchet assembly and to the drug delivery device, said inner barrel transmitting the stored torque from said first spring to the drug delivery device to increase an injection force thereof, wherein said ratchet assembly includes a lower ratchet and an upper ratchet, each of said lower and upper ratchets having a plurality of teeth for engagement therebetween.

15. The additive force device of claim 14, wherein
said first end of said first spring is secured to said ratchet assembly.

16. The additive force device for use with a drug delivery device of claim 1, wherein the plurality of teeth of the lower ratchet engage the plurality of teeth of the upper ratchet in an axial direction that is parallel to a centerline of the additive force device.

* * * * *